(12) United States Patent
Chen et al.

(10) Patent No.: US 12,338,140 B2
(45) Date of Patent: Jun. 24, 2025

(54) METHOD FOR REMOVING HEAVY METAL FROM WATER

(71) Applicant: NATIONAL CHUNG CHENG UNIVERSITY, Minsyong Township, Chiayi County (TW)

(72) Inventors: Chien-Yen Chen, Minsyong Township, Chiayi County (TW); Yi-Hsun Huang, Minsyong Township, Chiayi County (TW); Pin-Yun Lin, Minsyong Township, Chiayi County (TW); Anggraeni Kumala Dewi, Minsyong Township, Chiayi County (TW); Koyeli Das, Minsyong Township, Chiayi County (TW); Uttara Sukul, Minsyong Township, Chiayi County (TW); Tsung-Hsien Chen, Minsyong Township, Chiayi County (TW); Raju Kumar Sharma, Minsyong Township, Chiayi County (TW); Cheng-Kang Lu, Minsyong Township, Chiayi County (TW); Chung-Ming Lu, Minsyong Township, Chiayi County (TW)

(73) Assignee: National Chung Cheng University, Minsyong Township, Chiayi County (TW)

( * ) Notice: Subject to any disclaimer, the term of this patent is extended or adjusted under 35 U.S.C. 154(b) by 385 days.

(21) Appl. No.: 18/166,673

(22) Filed: Feb. 9, 2023

(65) Prior Publication Data
US 2024/0092662 A1   Mar. 21, 2024

(30) Foreign Application Priority Data
Sep. 16, 2022   (TW) .................................. 111135198

(51) Int. Cl.
*C02F 1/28*   (2023.01)
*B01J 20/02*   (2006.01)
(Continued)

(52) U.S. Cl.
CPC ........... *C02F 1/281* (2013.01); *B01J 20/0222* (2013.01); *C02F 1/5236* (2013.01); *C02F 1/62* (2013.01);
(Continued)

(58) Field of Classification Search
None
See application file for complete search history.

(56) References Cited

PUBLICATIONS

Hatayama et al. (Geomicrobiology Journal, 2020, 37, 603-609). (Year: 2020).*

(Continued)

*Primary Examiner* — Clare M Perrin
(74) *Attorney, Agent, or Firm* — Nixon & Vanderhye PC

(57) ABSTRACT

A method for removing a heavy metal from water includes subjecting a microbial solution containing a liquid culture of a urease-producing bacterial strain and a reaction solution containing a manganese compound and urea to a microbial-induced precipitation reaction, so as to obtain biomineralized manganese carbonate ($MnCO_3$) particles, admixing the biomineralized $MnCO_3$ particles with water containing a heavy metal, so that the biomineralized $MnCO_3$ particles adsorb the heavy metal in the water to form a precipitate, and removing the precipitate from the water.

13 Claims, 3 Drawing Sheets

(51) Int. Cl.
  *C02F 1/52* (2023.01)
  *C02F 1/62* (2023.01)
  *C12N 1/20* (2006.01)
  *C02F 101/10* (2006.01)
  *C02F 101/20* (2006.01)
  *C02F 101/22* (2006.01)

(52) U.S. Cl.
  CPC ............ *C12N 1/20* (2013.01); *B01J 20/0277* (2013.01); *C02F 2101/103* (2013.01); *C02F 2101/20* (2013.01); *C02F 2101/22* (2013.01)

(56) References Cited

PUBLICATIONS

Wu et al. (Microorganisms, 2022, 10, 2411). (Year: 2022).*
Cuaxinque-Flores et al. (Science of the Total Environment, 2020, 724, 138124). (Year: 2020).*
Achal et al. (Journal of Hazardous Materials, 2012, 201-202, pp. 178-184). (Year: 2012).*
Zhao et al. (Science of the Total Environment, 2021, 777, 146190). (Year: 2021).*
Fujita et al. (Geochimica et Cosmochimica Acta, 2004, 68, 3261-3270). (Year: 2004).*
Li et al. (International Biodeterioration & Biodegradation, 2013, 76, 81-85). (Year: 2013).*
Qian et al. (Journal of Cleaner Production, 2017, 164, 198-208). (Year: 2017).*
Hu et al. (Water Research, 2021, 190, 116753). (Year: 2021).*
Kang et al. (Ecological Engineering, 2016, 89, 64-69). (Year: 2016).*

\* cited by examiner

METHOD FOR REMOVING HEAVY METAL FROM WATER

CROSS-REFERENCE TO RELATED APPLICATION

This application claims priority of Taiwanese Invention Patent Application No. 111135198, filed on Sep. 16, 2022.

FIELD

The present disclosure relates to a method for removing a heavy metal from water.

BACKGROUND

Heavy metals, such as lead (Pb), zinc (Zn), mercury (Hg), nickel (Ni), cadmium (Cd), silver (Ag), iron (Fe), aluminum (Al), copper (Cu), chromium (Cr), and arsenic (As), are toxic and carcinogenic to organisms, and are non-biodegradable. Release of such heavy metals into the natural environment not only is harmful to the health of organisms, but also affects the balance of the ecosystem.

Methods for removing heavy metals from water include physical, chemical, and biological methods. Adsorption using synthetic adsorbents or natural adsorbents is the most commonly utilized physical method, and has the advantages of simple operation, low cost, and high efficiency.

In spite of the aforesaid, there is still a need for those skilled in the art to develop a method for removing a heavy metal from water, which can effectively adsorb heavy metals in water and is environmentally friendly.

SUMMARY

Therefore, the present disclosure provides a method for removing a heavy metal from water, which can alleviate at least one of the drawbacks of the prior art, and which includes:
(a) subjecting a microbial solution containing a liquid culture of a urease-producing bacterial strain and a reaction solution containing a manganese compound and urea to a microbial-induced precipitation reaction, so as to obtain biomineralized manganese carbonate ($MnCO_3$) particles;
(b) admixing the biomineralized $MnCO_3$ particles with water containing a heavy metal, so that the biomineralized $MnCO_3$ particles adsorb the heavy metal in the water to form a precipitate; and
(c) removing the precipitate from the water.

BRIEF DESCRIPTION OF THE DRAWINGS

Other features and advantages of the disclosure will become apparent in the following detailed description of the embodiment(s) with reference to the accompanying drawings. It is noted that various features may not be drawn to scale.

DETAILED DESCRIPTION

Figure 1:
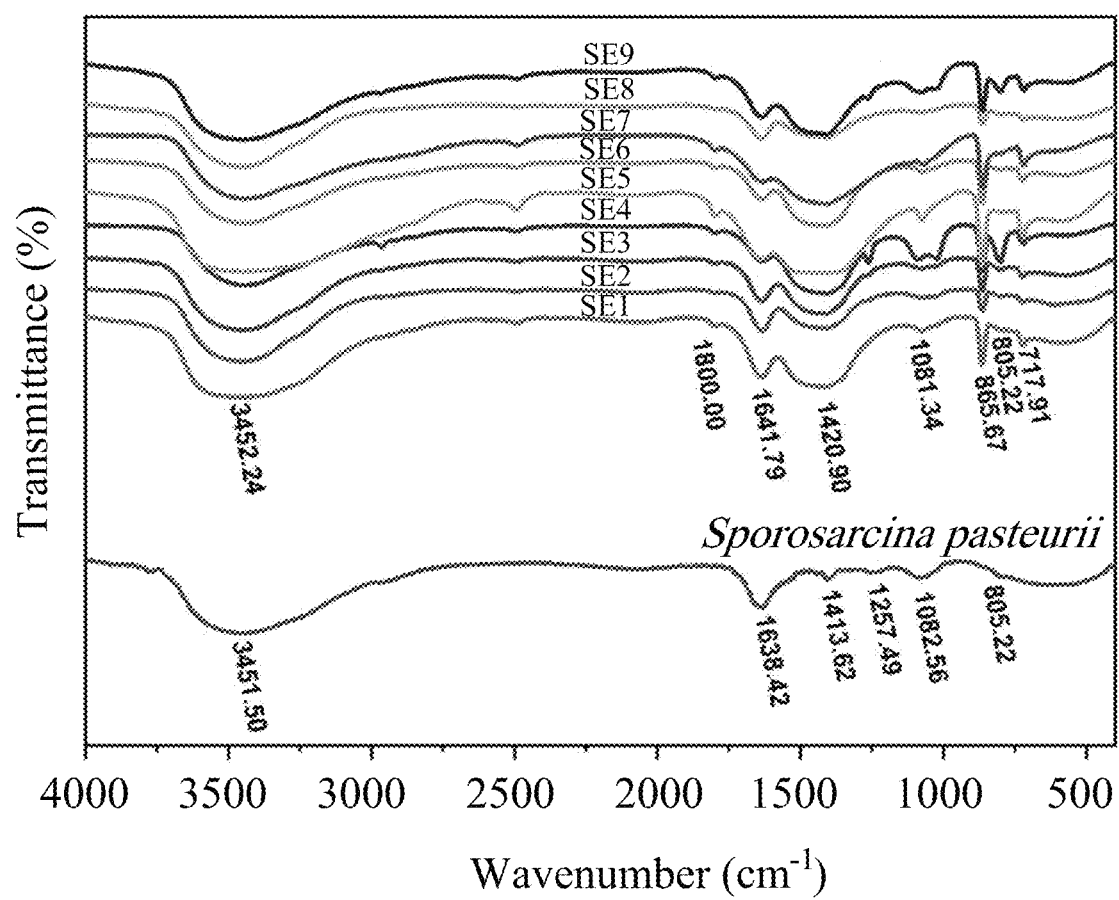
FIG. 1 shows the Fourier transform infrared spectroscopy (FTIR) spectra of the biomineralized $MnCO_3$ particles of SE1 to SE9 and the liquid culture of *Sporosarcina pasteurii*.

For the purpose of this specification, it will be clearly understood that the word "comprising" means "including but not limited to", and that the word "comprises" has a corresponding meaning.

It is to be understood that, if any prior art publication is referred to herein, such reference does not constitute an admission that the publication forms a part of the common general knowledge in the art, in Taiwan or any other country.

Unless defined otherwise, all technical and scientific terms used herein have the meaning commonly understood by a person skilled in the art to which the present disclosure belongs. One skilled in the art will recognize many methods and materials similar or equivalent to those described herein, which could be used in the practice of the present disclosure. Indeed, the present disclosure is in no way limited to the methods and materials described.

The present disclosure provides a method for removing a heavy metal from water, which includes:
(a) subjecting a microbial solution containing a liquid culture of a urease-producing bacterial strain and a reaction solution containing a manganese compound and urea to a microbial-induced precipitation reaction, so as to obtain biomineralized manganese carbonate ($MnCO_3$) particles;
(b) admixing the biomineralized $MnCO_3$ particles with water containing a heavy metal, so that the biomineralized $MnCO_3$ particles adsorb the heavy metal in the water to form a precipitate; and
(c) removing the precipitate from the water.

In certain embodiments, the urease-producing bacterial strain may be selected from the group consisting of *Sporosarcina* spp., *Proteus* spp., *Morganella* spp., *Serratia* spp., *Pseudomonas* spp., *Clostridium* spp., *Fusobacterium* spp., *Ureaplasma* spp., *Providencia* spp., *Sarcina* spp., *Lactobacillus* spp., *Streptococcus* spp., and combinations thereof. In an exemplary embodiment, the urease-producing bacterial strain is *Sporosarcina pasteurii* (also known as *Bacillus pasteurii*).

According to the present disclosure, the liquid culture of the urease-producing bacterial strain is prepared by culturing the abovementioned urease-producing bacterial strain in a liquid medium suitable for growth and/or proliferation thereof.

According to the present disclosure, the liquid medium, procedures, and conditions for culturing the urease-producing bacterial strain may be adjusted according to the urease-producing bacterial strain to be used, and are within the expertise and routine skills of those skilled in the art.

In certain embodiments, the liquid culture of the urease-producing bacterial strain has a bacterial concentration ranging from $10^5$ CFU/mL to $10^8$ CFU/mL, such that the biomineralized $MnCO_3$ particles formed therefrom can have an excellent removal rate of heavy metals.

In certain embodiments, the liquid culture of the urease-producing bacterial strain is present in an amount of 100% (v/v), based on the total volume of the microbial solution.

In certain embodiments, the liquid culture of the urease-producing bacterial strain is present in an amount ranging from 33% (v/v) to 67% (v/v), based on the total volume of the microbial solution.

According to the present disclosure, the manganese compound may be selected from the group consisting of manganese chloride ($MnCl_2$), manganese (II) nitrate ($Mn(NO_3)_2$), manganese (II) fluoride ($MnF_2$), manganese (II) bromide ($MnBr_2$), manganese (II) sulfate ($MnSO_4$), and combinations thereof. In certain embodiments, the manganese compound is $MnCl_2$ or hydrate thereof.

According to the present disclosure, in the reaction solution, the manganese compound may be present in a molar concentration ranging from 0.01 M to 1 M. In certain embodiments, in the reaction solution, the manganese compound is present in a molar concentration ranging from 0.1 M to 1 M, thereby increasing the yield of the biomineralized $MnCO_3$ particles. In an exemplary embodiment, in the reaction solution, the manganese compound is present in a molar concentration of 0.1 M, such that the biomineralized $MnCO_3$ particles formed therefrom can have an excellent removal rate of heavy metals.

According to the present disclosure, in the reaction solution, the urea may be present in a molar concentration ranging from 0.1 M to 1 M. In certain embodiments, in the reaction solution, the urea is present in a molar concentration of 1 M, such that the biomineralized $MnCO_3$ particles formed therefrom can have an excellent removal rate of heavy metals.

In an exemplary embodiment, the liquid culture of the urease-producing bacterial strain has a bacterial concentration ranging from $10^5$ CFU/mL to $10^8$ CFU/mL, and in the reaction solution, the manganese compound is present in a molar concentration of 0.1 M, the urea is present in a molar concentration of 1 M, such that the biomineralized $MnCO_3$ particles formed therefrom can have an excellent removal rate of heavy metals.

By virtue of the microbial-induced precipitation reaction in step (a), the urea is hydrolyzed by the urease-producing bacterial strain to form carbonate ions and ammonium ions, and then the carbonate ions react with the manganese ions provided by the manganese compound to form manganese carbonate crystals on the cell wall of the urease-producing bacterial strain, thereby obtaining the biomineralized $MnCO_3$ particles.

In certain embodiments, the biomineralized $MnCO_3$ particles have a mean particle size ranging from 2 μm to 5 μm.

In certain embodiments, the biomineralized $MnCO_3$ particles have a median particle size ranging from 2 μm to 5 μm.

It should be noted that, in comparison with the manganese carbonate obtained by chemical synthesis method or the manganese carbonate in the form of rhodochrosite, the biomineralized $MnCO_3$ particles formed by the microbial-induced precipitation reaction has a smaller particle size (i.e., a larger specific surface area), and hence can effectively adsorb heavy metals in water.

In certain embodiments, the microbial-induced precipitation reaction may be conducted for a time period ranging from 20 hours to 42.5 hours.

In certain embodiments, the heavy metal may be selected from the group consisting of cadmium, arsenic, chromium, copper, nickel, zinc, and combinations thereof.

According to the present disclosure, the precipitate may be removed from the water using techniques well-known to those skilled in the art. In certain embodiments, the precipitate is removed from the water by filtration.

According to the present disclosure, the biomineralized $MnCO_3$ particles formed by the microbial-induced precipitation reaction can serve as a heavy metal adsorbent and can effectively absorb heavy metals in water, so that the method of the present disclosure is simple and can effectively remove heavy metals in water.

The disclosure will be further described by way of the following examples. However, it should be understood that the following examples are solely intended for the purpose of illustration and should not be construed as limiting the disclosure in practice.

EXAMPLES

Urease-Producing Bacterial Strain:

*Sporosarcina pasteurii* (DSM33) used in the following experiments was purchased from the Bioresource Collection and Research Center (BCRC) of the Food Industry Research and Development Institute (FIRDI) (No. 331, Shih-Pin Rd., Hsinchu City 300, Taiwan).

ICP Multi-Element Standard Solution:

ICP multi-element standard solution (Cat. No. 1.09480.0100, Merck) used in the following experiments contained arsenic, copper, nickel, zinc, chromium, and cadmium, and the content of a respective one of the six metals was 5 ppm.

Preparation of Liquid Culture of *Sporosarcina pasteurii*:

1 mL of a inoculum of *Sporosarcina pasteurii* was inoculated in a culture medium containing 20 g of yeast extract (Becton, Dickinson and Company), 10 g of $(NH_4)_2SO_4$ (J. T. Baker), 0.13 M tris(hydroxymethyl)aminomethane (J. T. Baker), and 1000 ml of water, and was then cultivated in a shaking incubator (30° C., 180 rpm) for 48 hours, so as to obtain a liquid culture having a bacterial concentration ranging from $10^5$ CFU/mL to $10^8$ CFU/mL.

Synthesis Example 1 (SE1)

Appropriate amounts of urea and manganese chloride tetrahydrate ($MnCl_2 \cdot 4H_2O$) were dissolved in water, so as to obtain a reaction solution containing 1 M urea and 0.01 M manganese chloride ($MnCl_2$). 20 ml of ultrapure water was mixed with 10 ml of a liquid culture of *Sporosarcina pasteurii* to obtain a microbial solution. 15 mL of the reaction solution and 15 mL of the microbial solution were added into a screw-capped glass test tube, and then cultivated in a shaking incubator (29° C., 180 rpm) for 24 hours to allow a microbial-induced precipitation reaction to proceed, thereby obtaining a crude product containing biomineralized manganese carbonate ($MnCO_3$).

The crude product was washed with ultrapure water for several times, and then washed with ethanol for several times. After centrifugation at 10,000 rpm and 15° C. for 3.5 minutes, the resultant pellet was collected, and then subjected to a drying treatment in an oven (50° C.) for 48 hours, so as to obtain white-yellow biomineralized $MnCO_3$ particles.

Synthesis Examples 2 to 9 (SE2 to SE9)

The procedures for preparing the biomineralized $MnCO_3$ particles of SE2 to SE9 were similar to those of SE1, except that the concentration of the manganese chloride, and the amounts of the liquid culture of *Sporosarcina pasteurii* and the ultrapure water were varied as shown in Table 1 below.

TABLE 1

|  |  | SE |  |  |  |  |  |  |  |  |
|---|---|---|---|---|---|---|---|---|---|---|
|  |  | 1 | 2 | 3 | 4 | 5 | 6 | 7 | 8 | 9 |
| Reaction solution | MnCl₂ (M) | 0.01 | 0.01 | 0.01 | 0.1 | 0.1 | 0.1 | 1 | 1 | 1 |
|  | Urea (M) | 1 | 1 | 1 | 1 | 1 | 1 | 1 | 1 | 1 |
| Microbial solution | Liquid culture of *Sporosarcina pasteurii* (mL) | 10 | 20 | 30 | 10 | 20 | 30 | 10 | 20 | 30 |
|  | Ultrapure water (mL) | 20 | 10 | 0 | 20 | 10 | 0 | 20 | 10 | 0 |
| Biomineralized MnCO₃ particles | Yield (g) | 0.03 | 0.03 | 0.03 | 0.3 | 0.3 | 0.3 | 0.37 | 0.54 | 1.3 |
|  | Mean particle size (μm) | 3.56 | 3.10 | 3.52 | 2.86 | 3.06 | 2.75 | 4.70 | 4.46 | 4.19 |
|  | Median particle size (μm) | 3.59 | 3.00 | 3.44 | 2.83 | 3.00 | 2.69 | 4.64 | 4.39 | 4.05 |

Example 1 (EX1)

0.025 g of the biomineralized MnCO₃ particles of SE4 (serving as a heavy metal adsorbent) and 20 mL of the ICP multi-element standard solution (serving as a test sample) were placed into a screw-capped glass test tube, and then the resultant mixture was shaken in a shaking incubator (25° C., 160 rpm) for 48 hours, such that the biomineralized MnCO₃ particles of SE4 adsorbed the heavy metals in the ICP multi-element standard solution to form a precipitate.

Next, the mixture was subjected to a filtration treatment using a syringe filter (which was made of glass fiber and had a pore size of 0.2 μm) (Cat. No. 013N045I, Finetech) to remove the precipitate therefrom, thereby obtaining a filtrate.

Examples 2 to 6 (EX2 to EX6)

The procedures for preparing the filtrates of EX2 to EX6 were similar to those of EX1, except that the type of the biomineralized MnCO₃ particles was varied as shown in Table 2 below.

Property Evaluation:

A. Fourier Transform Infrared Spectroscopy (FTIR) Analysis

A respective one of the biomineralized MnCO₃ particles of SE1 to SE9 and the liquid culture of *Sporosarcina pasteurii* was subjected to FTIR analysis using a JASCO FT/IR-430 plus FT-IR spectrometer (wavenumber range: 4000 cm$^{-1}$ to 400 cm$^{-1}$).

Referring to FIG. 1, the FTIR spectrum of the respective one of the biomineralized MnCO₃ particles of SE1 to SE9 was different from that of the liquid culture of *Sporosarcina pasteurii*. In particular, the respective one of the biomineralized MnCO₃ particles of SE1 to SE9 had absorption bands at 1420.90 cm$^{-1}$, 865.67 cm$^{-1}$, 717.91 cm$^{-1}$ (which were attributed to MnCO₃), 1641.79 cm$^{-1}$ (which was attributed to the C=O bond of the carbonate group), and 805.22 cm$^{-1}$ (which was attributed to the liquid culture of *Sporosarcina pasteurii*).

B. X-Ray Diffraction (XRD) Analysis

A respective one of the biomineralized MnCO₃ particles of SE1 to SE9 was subjected to XRD analysis at a diffraction angle 2θ ranging from 20° to 40° using an X-ray diffractometer (Manufacturer: Shimadzu Corporation; Model no.: XRD-6000).

Figure 2:
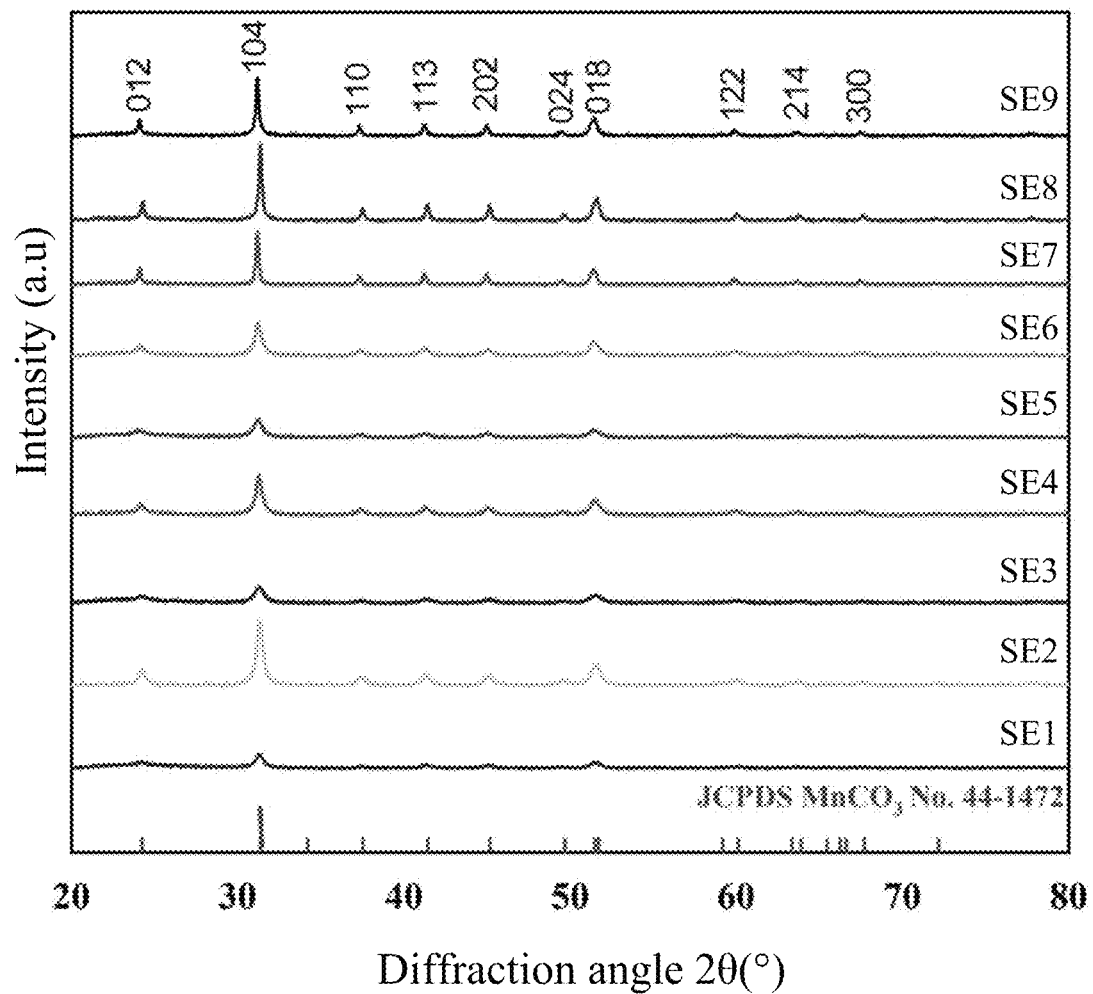
FIG. 2 is a graph showing the X-ray diffraction (XRD) patterns of the biomineralized $MnCO_3$ particles of SE1 to SE9.

Referring to FIG. 2, the respective one of the biomineralized MnCO₃ particles of SE1 to SE9 had diffraction peaks at 2θ angles of 24.198°, 31.271°, 37.505°, 41.287°, 45.068°, 49.586°, 51.548°, 59.969°, 63.751°, and 67.389°, which corresponded to the diffraction planes (012), (104), (110), (113), (202), (024), (018), (122), (214), and (300), respectively, and each of these ten diffraction peaks was in agreement with the pure rhombohedral MnCO₃ structure (JCPDS card No. 44-1472).

C. Field Emission Scanning Electron Microscopy (FESEM) Analysis

Figure 3:
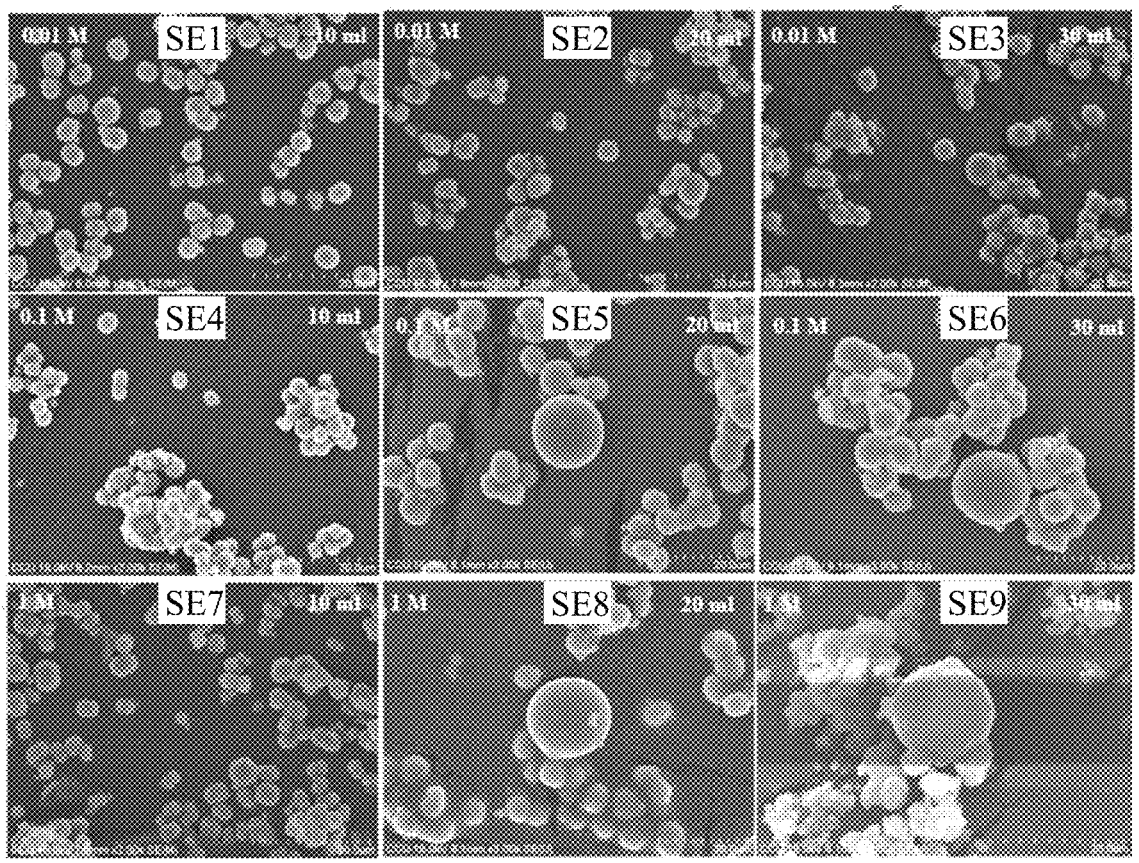
FIG. 3 shows the field emission scanning electron microscopy (FESEM) images of the biomineralized $MnCO_3$ particles of SE1 to SE9.

A respective one of the biomineralized MnCO₃ particles of SE1 to SE9 was subjected to FESEM analysis using a field emission scanning electron microscope (Manufacturer: Hitachi; Model no.: S-4800)(voltage: 15.0 kV). ImageJ software was used to analyze the particle size and particle size distribution (PSD) of the biomineralized MnCO₃ particles, so as to obtain the mean particle size and median particle size of the biomineralized MnCO₃ particles. The results are shown in FIGS. 3 and Table 1.

D. Inductively Coupled Plasma Optical Emission Spectroscopy (ICP-OES) Analysis

A respective one of the filtrates of EX1 to EX6 and the ICP multi-element standard solution was subjected to ICP-OES analysis using an Agilent 5100 ICP-OES spectrometer.

The heavy metal removal rate (%) was calculated using the following Equation (I):

$$A = [(B-C)/B] \times 100 \quad (I)$$

where
   A=heavy metal removal rate (%)
   B=metal content determined in the ICP multi-element standard solution (mg/L)
   C=metal content determined in the filtrate of respective Example (mg/L)

The results are shown in Table 2 below. It can be seen from Table 2 that the biomineralized MnCO₃ particles of SE4 to SE9 can remove nickel (Ni), cadmium (Cd), copper (Cu), chromium (Cr), and arsenic (As) from water, while the biomineralized MnCO₃ particles of SE4 to SE6 can also remove zinc (Zn) from water. In particular, the biomineralized MnCO₃ particles of SE4 to SE9 exhibit high removal efficiency for Cr and As in water, and the biomineralized MnCO₃ particles of SE4 to SE6 exhibit high removal efficiency for Cu and Cd in water.

It should be noted that, the biomineralized MnCO₃ particles of SE6 exhibit an excellent removal efficiency for Ni, Cd, Cu, Cr, As, and Zn, indicating that by virtue of the biomineralized MnCO₃ particles of SE6 having smaller mean particle size and median particle size (see Table 1), the biomineralized MnCO₃ particles of SE6 have a larger specific surface area, and hence can effectively adsorb heavy metals from water and exhibit excellent removal efficiency of heavy metal.

TABLE 2

| | | EX | | | | | |
|---|---|---|---|---|---|---|---|
| | | 1 | 2 | 3 | 4 | 5 | 6 |
| Biomineralized MnCO₃ particles | | SE4 | SE5 | SE6 | SE7 | SE8 | SE9 |
| Heavy metal removal rate (%) | Cd (%) | 65.9 | 86.3 | 88.0 | 30.7 | 30.0 | 24.7 |
| | As (%) | 99.1 | 99.1 | 99.1 | 98.9 | 98.8 | 98.9 |
| | Cr (%) | 95.6 | 96.8 | 97.0 | 96.3 | 96.3 | 94.7 |
| | Cu (%) | 89.0 | 94.3 | 94.7 | 50.9 | 48.2 | 38.6 |
| | Ni (%) | 15.2 | 17.6 | 29.5 | 7.1 | 10.5 | 12.3 |
| | Zn (%) | 18.4 | 42.9 | 48.6 | 0 | 0 | 0 |

In the description above, for the purposes of explanation, numerous specific details have been set forth in order to provide a thorough understanding of the embodiment(s). It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects; such does not mean that every one of these features needs to be practiced with the presence of all the other features. In other words, in any described embodiment, when implementation of one or more features or specific details does not affect implementation of another one or more features or specific details, said one or more features may be singled out and practiced alone without said another one or more features or specific details. It should be further noted that one or more features or specific details from one embodiment may be practiced together with one or more features or specific details from another embodiment, where appropriate, in the practice of the disclosure.

While the disclosure has been described in connection with what is (are) considered the exemplary embodiment(s), it is understood that this disclosure is not limited to the disclosed embodiment(s) but is intended to cover various arrangements included within the spirit and scope of the broadest interpretation so as to encompass all such modifications and equivalent arrangements.

What is claimed is:

1. A method for removing a heavy metal from water, comprising:
    (a) subjecting a microbial solution containing a liquid culture of a urease-producing bacterial strain and a reaction solution containing a manganese compound and urea to a microbial-induced precipitation reaction, so as to obtain biomineralized manganese carbonate (MnCO₃) particles;
    (b) admixing the biomineralized MnCO₃ particles with water containing a heavy metal, so that the biomineralized MnCO₃ particles adsorb the heavy metal in the water to form a precipitate; and
    (c) removing the precipitate from the water.

2. The method as claimed in claim 1, wherein the biomineralized MnCO₃ particles have a mean particle size ranging from 2 μm to 5 μm.

3. The method as claimed in claim 1, wherein the biomineralized MnCO₃ particles have a median particle size ranging from 2 μm to 5 μm.

4. The method as claimed in claim 1, wherein the heavy metal is selected from the group consisting of cadmium, arsenic, chromium, copper, nickel, zinc, and combinations thereof.

5. The method as claimed in claim 1, wherein in the reaction solution, the manganese compound is present in a molar concentration ranging from 0.01 M to 1 M.

6. The method as claimed in claim 1, wherein the liquid culture of the urease-producing bacterial strain has a bacterial concentration ranging from $10^5$ CFU/mL to $10^8$ CFU/mL.

7. The method as claimed in claim 6, wherein the liquid culture of the urease-producing bacterial strain is present in an amount of 100% (v/v), based on the total volume of the microbial solution.

8. The method as claimed in claim 6, wherein the liquid culture of the urease-producing bacterial strain is present in an amount ranging from 33% (v/v) to 67% (v/v), based on the total volume of the microbial solution.

9. The method as claimed in claim 1, wherein the microbial-induced precipitation reaction is conducted for a time period ranging from 20 hours to 42.5 hours.

10. The method as claimed in claim 1, wherein in the reaction solution, the urea is present in a molar concentration ranging from 0.1 M to 1 M.

11. The method as claimed in claim 1, wherein the urease-producing bacterial strain is selected from the group consisting of *Sporosarcina* spp., *Proteus* spp., *Morganella* spp., *Serratia* spp., *Pseudomonas* spp., *Clostridium* spp., *Fusobacterium* spp., *Ureaplasma* spp., *Providencia* spp., *Sarcina* spp., *Lactobacillus* spp., *Streptococcus* spp., and combinations thereof.

12. The method as claimed in claim 11, wherein the urease-producing bacterial strain is *Sporosarcina* pasteurii.

13. The method as claimed in claim 1, wherein the manganese compound is selected from the group consisting of manganese chloride (MnCl₂), manganese (II) nitrate (Mn(NO₃)₂), manganese (II) fluoride (MnF₂), manganese (II) bromide (MnBr₂), manganese (II) sulfate (MnSO₄), and combinations thereof.

* * * * *